(12) United States Patent
Shaner, Sr.

(10) Patent No.: US 11,766,359 B1
(45) Date of Patent: Sep. 26, 2023

(54) SLEEP MASK HAVING EAR LOOPS

(71) Applicant: Michael Christopher Shaner, Sr., Memphis, TN (US)

(72) Inventor: Michael Christopher Shaner, Sr., Memphis, TN (US)

(*) Notice: Subject to any disclaimer, the term of this patent is extended or adjusted under 35 U.S.C. 154(b) by 0 days.

(21) Appl. No.: 16/408,528

(22) Filed: May 10, 2019

(51) Int. Cl.
*A61F 9/04* (2006.01)

(52) U.S. Cl.
CPC ..................... *A61F 9/04* (2013.01)

(58) Field of Classification Search
CPC ......... A61F 9/04; A47G 9/10; A41D 13/1184; A61B 6/107; A61B 6/14
USPC ........................................................ 2/15, 209
See application file for complete search history.

(56) References Cited

U.S. PATENT DOCUMENTS

| | | | | |
|---|---|---|---|---|
| 1,799,064 A * | 3/1931 | Rickerd | ..................... | A61F 9/02 2/12 |
| 1,924,315 A * | 8/1933 | Hemphill | ................... | A61F 9/04 2/15 |
| 2,243,982 A * | 6/1941 | Seeley | ...................... | A61F 9/04 2/12 |
| 4,908,878 A * | 3/1990 | Tarragano | ................. | A61F 9/04 128/206.13 |
| 5,425,380 A * | 6/1995 | Hudson | .................... | A61F 9/026 128/858 |
| 6,543,056 B2 * | 4/2003 | Spiteri | ...................... | A61F 9/04 2/15 |
| 7,058,992 B1 * | 6/2006 | Ogonowsky | ............ | A61F 9/027 2/209 |
| 10,406,035 B1 * | 9/2019 | Scott | ......................... | A61F 9/04 |
| 2013/0255697 A1 * | 10/2013 | Thompson | ................ | A61F 9/04 128/858 |

\* cited by examiner

Primary Examiner — Katherine M Moran

(57) ABSTRACT

A sleep mask having ear loops to prevent unwanted movement on the user while sleeping. The sleep mask having ear loops that can be positioned behind and around the user's ear to prevent shifting during sleep. The sleep mask includes an eye cover that covers both eyes of the user to prevent light from reaching the user's eyes. The resistance strap provides resistance to the back of the ear for maximum security. The eye covers and strap are uniform in fabric and fit securely over the head and using the ear loops to secure the device in place.

1 Claim, 2 Drawing Sheets

SLEEP MASK HAVING EAR LOOPS

BACKGROUND OF THE INVENTION

Field of the Invention

The present invention relates to sleep masks. More specifically, the present invention provides a sleep mask having ear loops so as to prevent unwanted movement, particularly when the user is trying to sleep.

Many people toss and turn throughout the night for various reasons causing a sleep mask to shift around on the user. Some people will adjust their sleep position numerous times before finding a comfortable position to sleep. Other people are commonly roused from sleep due to being uncomfortable and shift around causing the mask to move during the night.

While conventional sleep masks may be adjustable or come with a strap, such masks do not remain secure without discomfort to the user. Adjustments can be made with other masks that tighten around the user at the cost of comfort. If the mask is tightened it can create soreness over prolonged wear. Thus a sleep mask that fits over a user's head and secured in place with ear loops.

Other similar devices may have other components composed of a hard material such as plastic. Sleeping on these hard components will cause the user to be aroused from sleep during the night and require adjustments.

These prior art devices have several known drawbacks. The devices in the prior art relate to headgear to be worn while sleeping for providing eye covers the user. Some such devices additionally help to alleviate problems such as sleep apnea and snoring. However, these devices do not often fit securely without discomfort.

In light of the devices disclosed in the prior drawings, it is submitted that the present invention substantially diverges in security elements from the prior art and consequently it is clear that there is a need in the art for an improvement to existing sleep mask devices. In this regard the instant invention substantially fulfills these needs.

SUMMARY OF THE INVENTION

In view of the foregoing disadvantages inherent in the known types of sleeping headgear now present in the drawings, the present invention provides a new sleep mask device wherein the same can be utilized for providing secure comfort when preventing a device from shifting on the user.

It is therefore an object of the present invention to provide a new and improved sleep mask comprising of ear loops for remaining securely in place while covering both eyes of the user.

It is another object of the present invention to provide a sleep mask further comprising a pair of ear loops adapted to be placed behind the user's ears in order to prevent the device from shifting on the user.

Another object of the present invention is to provide a sleep mask comprising a strap that is uniform to the eye covers and is fitted over the user's head and secured by the ear loops.

Yet another object of the present invention is to provide a sleep mask fit to size and adjustable via soft elastic fabric.

Another object of the present invention is to provide a sleep mask that may be readily fabricated from materials that permit comfort and are commensurate with durability and elasticity.

Other objects, features and advantages of the present invention will become apparent from the following detailed description taken in conjunction with the accompanying drawings.

BRIEF DESCRIPTIONS OF THE DRAWINGS

Although the characteristic features of this invention will be specifically pointed out in the claims, the invention itself and manner in which it may be made and used may be better understood after a review of the following description, taken in connection with the accompanying drawings wherein like numeral annotations are provided throughout.

FIG. 1 shows a frontal view of the sleep mask as worn by a user.

FIG. 2 shows a lateral view of the sleep mask having ear loops.

DETAILED DESCRIPTION OF THE INVENTION

Figure 1:
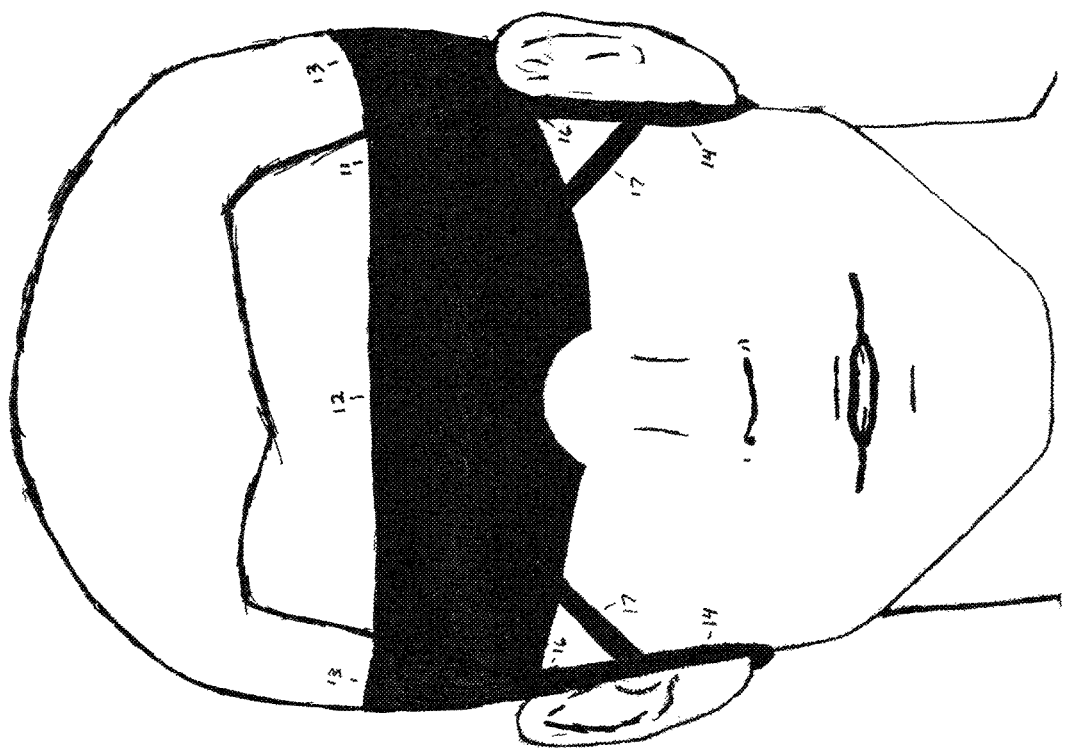
FIG. 1 shows a frontal view of the sleep mask having ear loops.

Reference is made herein to the attached drawings. Like reference numerals are used throughout the drawings to depict like or similar elements of the sleep mask. For the purposes of presenting a brief and clear description of the present invention, the preferred embodiment will be discussed as used for preventing shifting around while sleeping. The figures are intended for representative purposes only and should not be considered to be limiting in any respect.

Referring now to FIG. 1, there is shown a frontal view of the sleep mask 11 having ear loops 14. The sleep mask 11 comprises an eye cover 12 adapted to be positioned over the eyes of the user. The eye cover 12 is preferably shaped so as to cover both eyes of the user. In the illustrated embodiment, the eye cover 12 comprises a unitary body having a recessed lower end so that the eye cover 12 does not extend onto the user's nose.

The sleep mask 11 is preferably composed of a soft, flexible material so that the eye cover 12 conforms to the shape of the user's face. Thus, in some embodiments, the sleep mask 11 is composed of a fabric material, such as cotton or fleece. Further, the eye cover 12 is composed of an opaque material that prevents light from passing through. The eye cover 12 may further include padding to provide comfort to the user.

An eye cover strap 13 having no end, connects to the eye cover 12, wherein the eye cover strap 13 forms a loop that can be disposed over the user's head so as to secure the eye cover 12 in position over the user's eyes. In some embodiments, the eye cover strap 13 comprises an elastic material so that the eye cover strap 13 can be stretched into position over the user's head. Ear loops 14 that fit around the user's ears so the device fits comfortably and securely.

Figure 2:
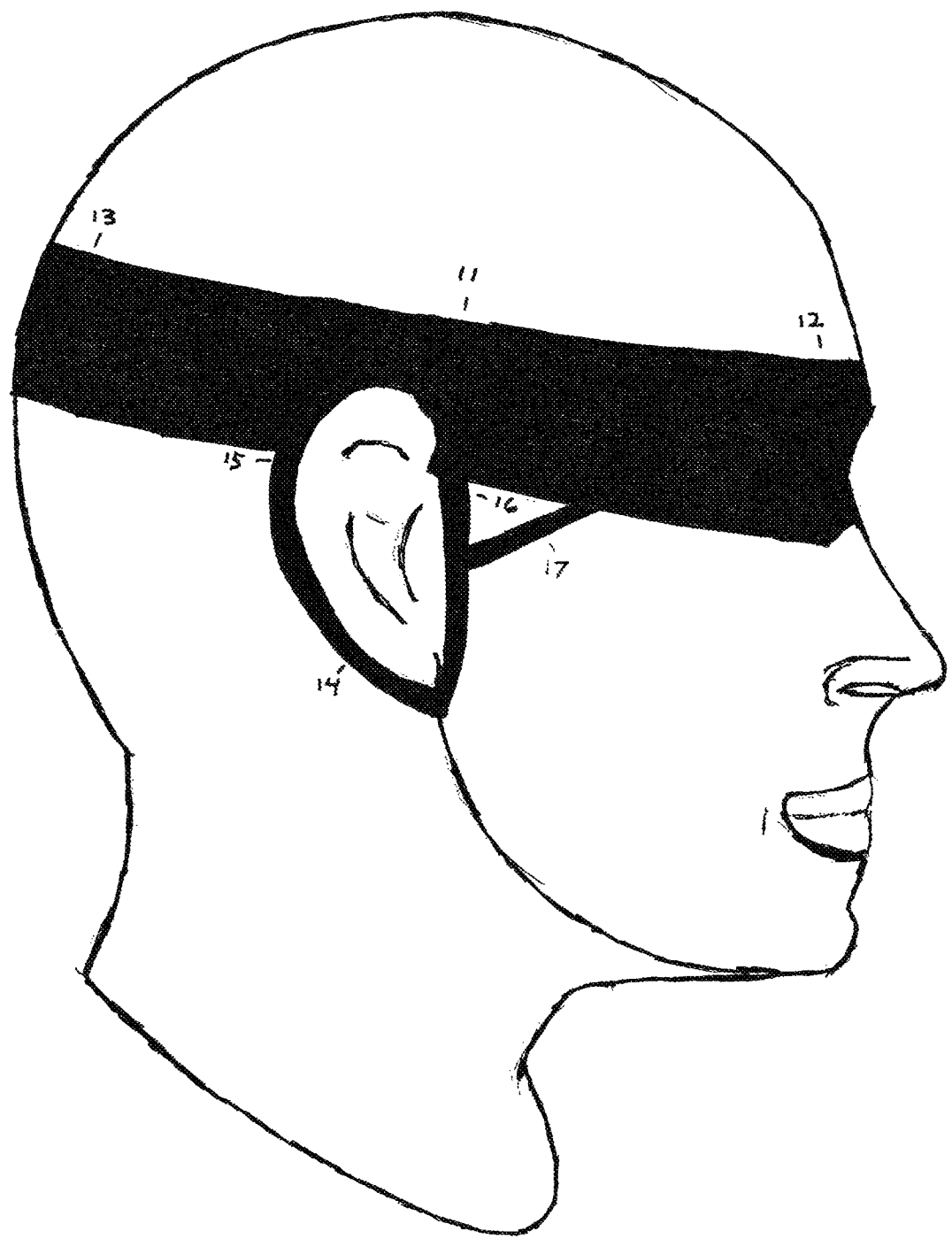
FIG. 2 shows a lateral view of ear loops of the sleep mask as worn by a user.

Referring now to FIG. 2, there is shown a perspective view of a lateral embodiment of the eye cover 12, the eye cover strap 13, and ear loops 14 of the sleep mask. In the illustrated embodiment, the ear loop is enveloped behind the user's ear to allow the device to remain securely in place.

The sleep mask 11 further comprises a pair of ear loops 14. An ear loop 14 includes a first end 15 and a second end 16, connected to the sleep mask 11 wherein an ear loop 14 is positioned around the user's ear. The ear loop 14 is preferably composed of the same material as the device so that it remains comfortable and securely positioned on the user's head.

Referring to FIG. 2, there is shown a lateral view of the ear loop 14 of the sleep mask. The ear loop 14 preferably comprises a soft material and is sized so as to be fully comfortable to a user's ear. The ear loops 14 may be composed of one or more layers of fabric in order to provide more comfort to the user. It is not desired to limit the exact construction of the ear loops 14.

Referring to FIG. 2 once again, there is shown a close up lateral view of the sleep mask as worn by a user. The ear loops 14 restrict tension and add security so as to keep the sleep mask 11 in position over the user's head comfortably. The ear loops 14 help to prevent the device from unwanted movement on the user during the night and a resistance strap 17 provides resistance on the ear loops 14 to enhance the retention features of the ear loops 14.

The user can position the sleep mask 11 over his or her head. To secure the device in place, the user positions the ear loops 14 around the back of his or her ears so as to secure the sleep mask 11 in position. To provide further securement, the eye cover strap 13 wraps around the user's head. This allows the device to remain securely in place if the user shifts around during sleep.

It is therefore submitted that the instant invention has been shown and described in what is considered to be the most practical and preferred embodiments for security. It is recognized, however, that departures or additions may be made within the scope of the invention and that modifications will occur to a person skilled in the art. With respect to the above description, it is to be realized that the optimum dimensional specifications for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative of the principles of the invention. Further, since modifications and changes can readily occur to those skilled in the art, it is not desired to limit the invention to the exact construction and operation shown and described, and accordingly, all suitable modifications and equivalents may be resorted to, falling within the scope of the invention.

The invention claimed is:

1. A sleep mask comprising: an opaque fabric eye cover (12) adapted to be positioned over eyes of a user, said opaque fabric eye cover (12) comprising a unitary body and a recessed lower edge such that the lower edge is configured to accommodate the user's nose, an eye cover strap (13) connected to the eye cover (12), said eye cover strap (13) forming a loop configured to wrap around the user's head for securing the eye cover (12) in position over the user's eyes, a pair of fabric ear loops (14), each ear loop (14) having a first end (15) and a second end (16) connected to the sleep mask and each ear loop (14) extending downwardly from the sleep mask on a lateral side thereof such that a back portion of each ear loop (14) is configured to wrap around a back of the user's ear, and a front portion of each ear loop (14) is configured to align with a front of the user's ear, a pair of resistance straps (17), each resistance strap (17) having a first end and a second end, with a first end connected to the eye cover (12) and the second end connected to the front portion of each ear loop (14) on each lateral side of the sleep mask, said ear loops configured to retain the sleep mask (11) in position on the user's head.

* * * * *